United States Patent
Cheng et al.

(10) Patent No.: US 10,779,735 B2
(45) Date of Patent: Sep. 22, 2020

(54) IMAGE-PROCESSING METHODS FOR MARKING PLAQUE FLUORESCENT REACTION AREA AND SYSTEMS THEREFOR

(71) Applicant: Quanta Computer Inc., Taoyuan (TW)

(72) Inventors: Kai-Ju Cheng, Taoyuan (TW); Chin-Yuan Ting, Taoyuan (TW); Hsin-Lun Hsieh, Taoyuan (TW); Tsung-Hsin Lu, Taoyuan (TW); Yu-Hsun Chen, Taoyuan (TW); Hao-Ping Lee, Taoyuan (TW)

(73) Assignee: QUANTA COMPUTER INC., Guishan Dist., Taoyuan (TW)

( * ) Notice: Subject to any disclaimer, the term of this patent is extended or adjusted under 35 U.S.C. 154(b) by 116 days.

(21) Appl. No.: 16/137,585

(22) Filed: Sep. 21, 2018

(65) Prior Publication Data
US 2020/0022582 A1     Jan. 23, 2020

(30) Foreign Application Priority Data
Jul. 23, 2018    (TW) .............................. 107125326 A

(51) Int. Cl.
*A61B 5/00*    (2006.01)
*A61B 6/14*    (2006.01)
(Continued)

(52) U.S. Cl.
CPC .......... *A61B 5/0088* (2013.01); *A61B 5/0013* (2013.01); *A61B 5/4547* (2013.01);
(Continued)

(58) Field of Classification Search
CPC ... A61B 5/0088; A61B 5/0013; A61B 5/4547; A61B 6/14; A61B 6/501; A61C 9/0046
(Continued)

(56) References Cited

U.S. PATENT DOCUMENTS

2015/0286044 A1* 10/2015 Rout .................... G02B 21/367
                                                                348/79
2016/0125601 A1    5/2016 Wu et al.
(Continued)

FOREIGN PATENT DOCUMENTS

JP    2011182993 A    9/2011
WO   2016/073569 A2   5/2016

OTHER PUBLICATIONS

European Search Report dated Jan. 11, 2019, issued in application No. 18202629.4.

*Primary Examiner* — Michael R Neff
(74) *Attorney, Agent, or Firm* — McClure, Qualey & Rodack, LLP

(57) ABSTRACT

An image-processing method for marking plaque fluorescent reaction areas is provided, including: obtaining a first RGB image of a mouth region; obtaining a second RGB image of the mouth region; respectively converting the first RGB image and the second RGB image into a first HSV image and a second HSV image; obtaining a first average brightness value of the first HSV image and a second average brightness value of the second HSV image; normalizing the first average brightness value or the second average brightness value according the first average brightness value and the second average brightness value to obtain a normalized image; converting the normalized image into a third RGB image, and obtaining a plurality of pixel points of the dental plaque according to the third RGB image and the first RGB image or the second RGB image; and marking the pixel points in the third RGB image.

10 Claims, 3 Drawing Sheets

(51) Int. Cl.
*A61B 6/00* (2006.01)
*A61C 9/00* (2006.01)

(52) U.S. Cl.
CPC ............... *A61B 6/14* (2013.01); *A61B 6/501* (2013.01); *A61C 9/0046* (2013.01)

(58) Field of Classification Search
USPC ......................................................... 382/154
See application file for complete search history.

(56) References Cited

U.S. PATENT DOCUMENTS

2017/0172418 A1\* 6/2017 Munro ................. A61B 5/0088
2017/0319057 A1\* 11/2017 Inglese .............. A61B 1/00009
2017/0330360 A1\* 11/2017 Higashi ................ G06T 11/001

\* cited by examiner

IMAGE-PROCESSING METHODS FOR MARKING PLAQUE FLUORESCENT REACTION AREA AND SYSTEMS THEREFOR

CROSS REFERENCE TO RELATED APPLICATIONS

This application claims priority of Taiwan Patent Application No. 107125326, filed on Jul. 23, 2018, the entirety of which is incorporated by reference herein.

BACKGROUND OF THE INVENTION

Field of the Invention

The present invention relates to an image-processing method for marking plaque fluorescent reaction areas and a system therefor, and more particularly to an image-processing method a system for more accurately marking areas having plaque by comparing two oral images corresponding to two different light sources and adjusting the brightness values of two oral images.

Description of the Related Art

With the improvement of people's living standards, people pay more and more attention to dental hygiene. Periodontal disease is a common dental disease, and the important factors causing periodontal disease are calculus and plaque. In order to prevent periodontal disease, if the location of plaque can be marked on the teeth during cleaning, the effectiveness of cleaning teeth can be improved. Therefore, how to easily and accurately find an area having plaque is a problem that needs to be solved.

BRIEF SUMMARY OF INVENTION

An embodiment of the present invention provides an image-processing method for marking plaque fluorescent reaction areas, the steps of which include: emitting, via a first light emitter, natural light to a mouth region of a user; obtaining, via an image-capturing unit, a first RGB image corresponding to the mouth region; emitting, via a second light emitter, blue light to the mouth region; obtaining, via the image-capturing unit, a second RGB image corresponding to the mouth region; converting, via a processing unit, the first RGB image and the second RGB image into a first HSV image and a second HSV image respectively; obtaining, via the processing unit, a first average brightness value corresponding to the first HSV image and a second average brightness value corresponding to the second HSV image; normalizing, via the processing unit, one of the first average brightness value and the second average brightness value with the other one of the first average brightness value and the second average brightness value to obtain a normalized image; converting, via the processing unit, the normalized image into a third RGB image, and obtaining a plurality of pixel points corresponding to the plaque according to the third RGB image and the first RGB image or the second RGB image; and marking the pixel points in the third RGB image.

Another embodiment of the present invention provides a system for marking plaque fluorescent reaction areas, including a first light emitter, a second light emitter, and image-capturing unit, a processing unit and a display unit. The first light emitter emits natural light to a mouth region of a user. The second light emitter emits blue light to the mouth region. The image-capturing unit obtains a first RGB image corresponding to the natural light and a second RGB image corresponding to the blue light. The processing unit converts the first RGB image into a first HSV image and the second RGB image into a second HSV image, obtains a first average brightness value corresponding to the first HSV image and a second average brightness value corresponding to the second HSV image, normalizes one of the first average brightness value and the second average brightness value with the other one of the first average brightness value and the second average brightness value to obtain a normalized image, converts the normalized image into a third RGB image, and obtains a plurality of pixel points corresponding to the plaque according to the third RGB image and the first RGB image or the second RGB image. The display unit displays and marks the pixel points in the third RGB image.

BRIEF DESCRIPTION OF DRAWINGS

The invention can be more fully understood by reading the subsequent detailed description and examples with references made to the accompanying drawings, wherein.

DETAILED DESCRIPTION OF INVENTION

Further areas to which the present image-processing methods for marking plaque fluorescent reaction areas and systems therefore can be applied will become apparent from the detailed description provided herein. It should be understood that the detailed description and specific examples, while indicating exemplary embodiments of the image-processing methods and the systems, are intended for the purposes of illustration only and are not intended to limit the scope of the invention.

Figure 1:
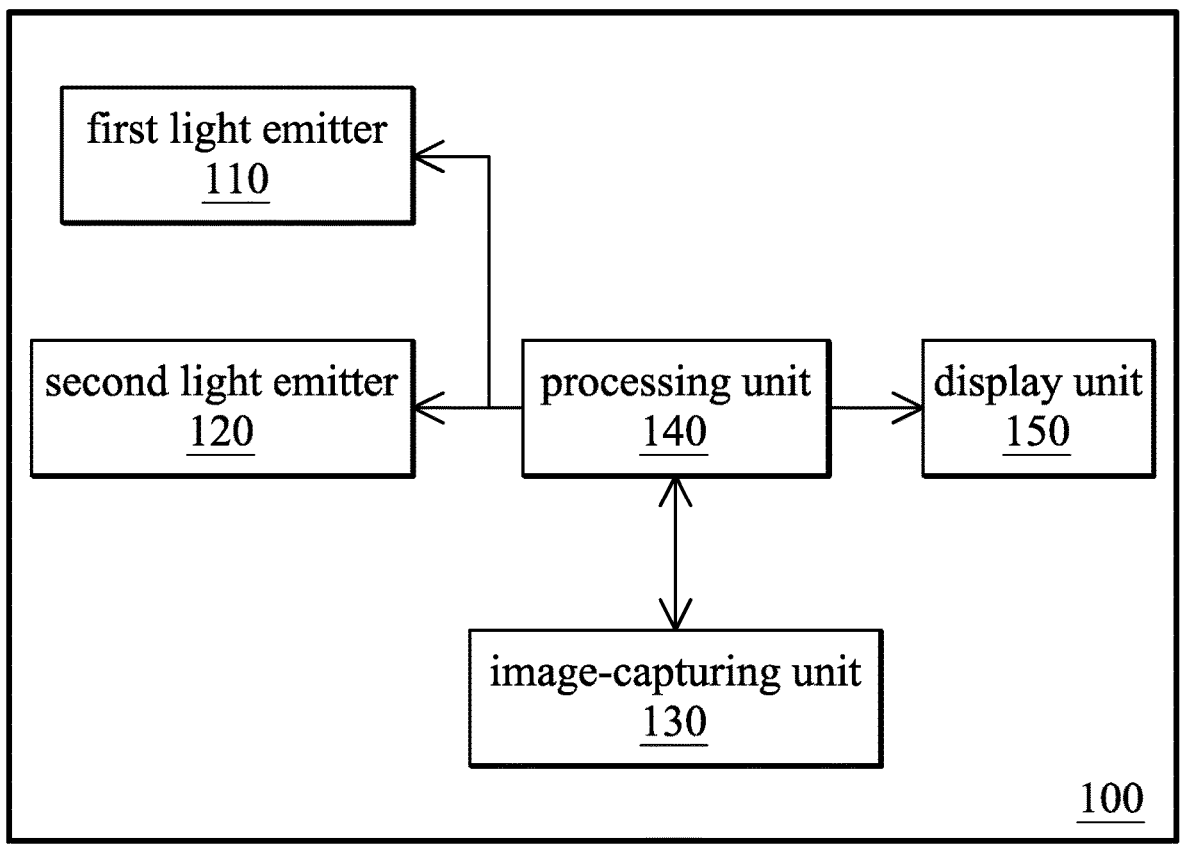
FIG. 1 is a system architecture diagram of a system for marking plaque fluorescent reaction areas in accordance with an embodiment of the present invention.

FIG. 1 is a system architecture diagram of a system for marking plaque fluorescent reaction areas in accordance with an embodiment of the present invention. As shown in FIG. 1, the system 100 at least includes a first light emitter 110, a second light emitter 120, an image-capturing unit 130, a processing unit 140, and a display unit 150. The first light emitter 110 is configured to emit natural light to an oral region of a user. The second light emitter 120 is configured to emit blue light to the oral region of the user. In an embodiment of the invention, a wavelength of the blue light is less than 480 nm, but it can be adjusted according to the needs of the implementation, so that the fluorescence reaction corresponding to the plaque can be more remarkable. Alternatively, the second light emitter 120 can also selectively emit other light that can causes plaque to produce a fluorescent response, and it is not limited to the blue light described herein.

The image-capturing unit 130 can be a lens for capturing RGB images of the oral region after the first light emitter 110 and the second light emitter 120 emit natural light and blue light to the oral region. The processing unit 140 is configured to convert the RGB images into HSV images expressed in Hue, Saturation and brightness, and calculate an average brightness value of each of the HSV images, and correct the HSV image with a lower brightness value to obtain a normalized image. The processing unit 140 further compares the RGB images and the HSV images corresponding to different light sources to obtain pixel points corresponding to the plaque. The processing unit 140 can be implemented in a variety of ways, for example, in a dedicated hardware circuit or general hardware, such as a single processor, a multiprocessor with parallel processing capability, a graphics processor, or another processor with computational capabilities. When the processing unit 140 executes code or software, it performs the functions described below. The display unit 150 can be a display panel, such as a thin film liquid-crystal display panel, an organic light-emitting diode panel, or another type of display panel, for displaying oral images having plaque fluorescent reaction areas for the user. In addition, the system 100 further includes a storage unit which is not shown in FIG. 1. The storage unit can be a non-volatile storage device such as a hard disk or a flash drive for storing instructions related to the method described below and the RGB images and the HSV images obtained for the processing unit 140.

According to an embodiment of the invention, after the first light emitter 110 emits the natural light and the second light emitter 120 emits the blue light, the processing unit 140 causes the image-capturing unit 130 to obtain a first RGB image corresponding to the natural light and a second RGB image corresponding to the blue light. After obtaining the first RGB image and the second RGB image, the processing unit 140 converts the first RGB image into a first HSV image and converts the second RGB image into a second HSV image having the brightness information, respectively. The processing unit 140 further obtains a first average brightness values corresponding to the first HSV image and a second average brightness value corresponding to the second HSV images. The average brightness value described herein represents the average brightness value of each pixel in each HSV image. It should be noted that, converting the RGB image into the HSV image is only an example of the present invention. In other embodiments, the processing unit 140 can also convert the RGB image into a LAB color space or an HSL color space, etc., and it is not limited thereto. Furthermore, the processing unit 140 compares the first average brightness value and the second average brightness value, and normalizes the brightness value of the smallest one by using the largest one to obtain a normalized image.

For example, in an embodiment of the present invention, the first average brightness value of the first HSV image corresponding to the natural light is 0.41036, and the second average brightness value of the second HSV image corresponding to the blue light is 0.13569. Since the second average brightness value corresponding to the blue light is less than the first average brightness value corresponding to the natural light, the processing unit 140 normalizes each pixel point in the second HSV image corresponding to the blue light. Using a single pixel as an example, a red value, a green value, and a blue value of the pixel in the second RGB image are (46, 18, 41), and after being converted into the HSV color space by the processing unit 140, the values corresponding to hue (h), saturation (s), and brightness (v) are (310.7143, 0.60870, 0.18039). When the processing unit 140 normalizes the image, the brightness value is multiplied by a ratio of the first average brightness value to the second average brightness value, and then multiplied by a predetermined parameter value to obtain the normalized image. The predetermined parameter value is used to optimize the normalized image, so that the area of the plaque is more visible. It should be noted that the user can also selectively not multiply the predetermined parameter value. Using the pixel point described above as an example, the predetermined parameter value is preset to ⅔, that is, the normalized brightness value is v'=0.18039*(0.41036/0.13569)*(⅔) =0.36370. In other words, after the normalization process, the values corresponding to the hue (h), the saturation (s), and the brightness (v) of the pixel point are (310.7143, 0.60870, 0.36370).

Next, the processing unit 140 converts the normalized image back to the RGB image to obtain a third RGB image. Using the pixel point described above as an example, after the normalized image is converted, the red value, the green value, and the blue value are (92, 36, 82), that is, compared to the original second RGB image, the red value, the green value, and the blue value become larger because the brightness value corresponding to each pixel has been increased.

After obtaining the normalized image and the third RGB image, the processing unit 140 determines whether the pixel is a pixel corresponding to the plaque (i.e. which may has the fluorescent reaction to the blue light) according to the red value, the green value, the blue value and the brightness value. The condition for determining whether the pixel is the pixel that corresponds to the plaque includes determining whether the red value is greater than the green value and the blue value, whether the brightness value is greater than the product of a largest average brightness value and the predetermined parameter value, and whether the red value is greater than the red value of an HSV image having the largest average brightness value. Using the pixel point described above as an example, the red value (92) is greater than the green value (36) and the blue value (82), and the brightness value (0.36370) is greater than the product of the first average brightness value and the predetermined parameter value (0.41036*(⅔)=0.27357), and the red value (92) is greater than the red value (90) of the pixel in the first RGB image. Because the fluorescent reaction of the plaque only generated under the blue light, the red teeth, lips and other areas can be excluded from the original RGB images by determining whether the red value of the normalized image is greater than the red value of the original RGB images. Next, the processing unit 140 marks the pixel as the pixel that corresponds to the plaque, and displays it in the third RGB image through a specific color value. Finally, after the processing unit 140 processes each pixel of the second HSV image, the third RGB image indicating a plurality of pixels corresponding to the plaque can be obtained, and it can be displayed through the display unit 150.

According to another embodiment of the present invention, because the first RGB image and the second RGB image are obtained at different time points, after the processing unit 140 normalizes the HSV image, the processing unit 140 can further perform a Harris corner detection algorithm, Detection/SIFT to correct the position of the two images to avoid errors.

Figure 2A:
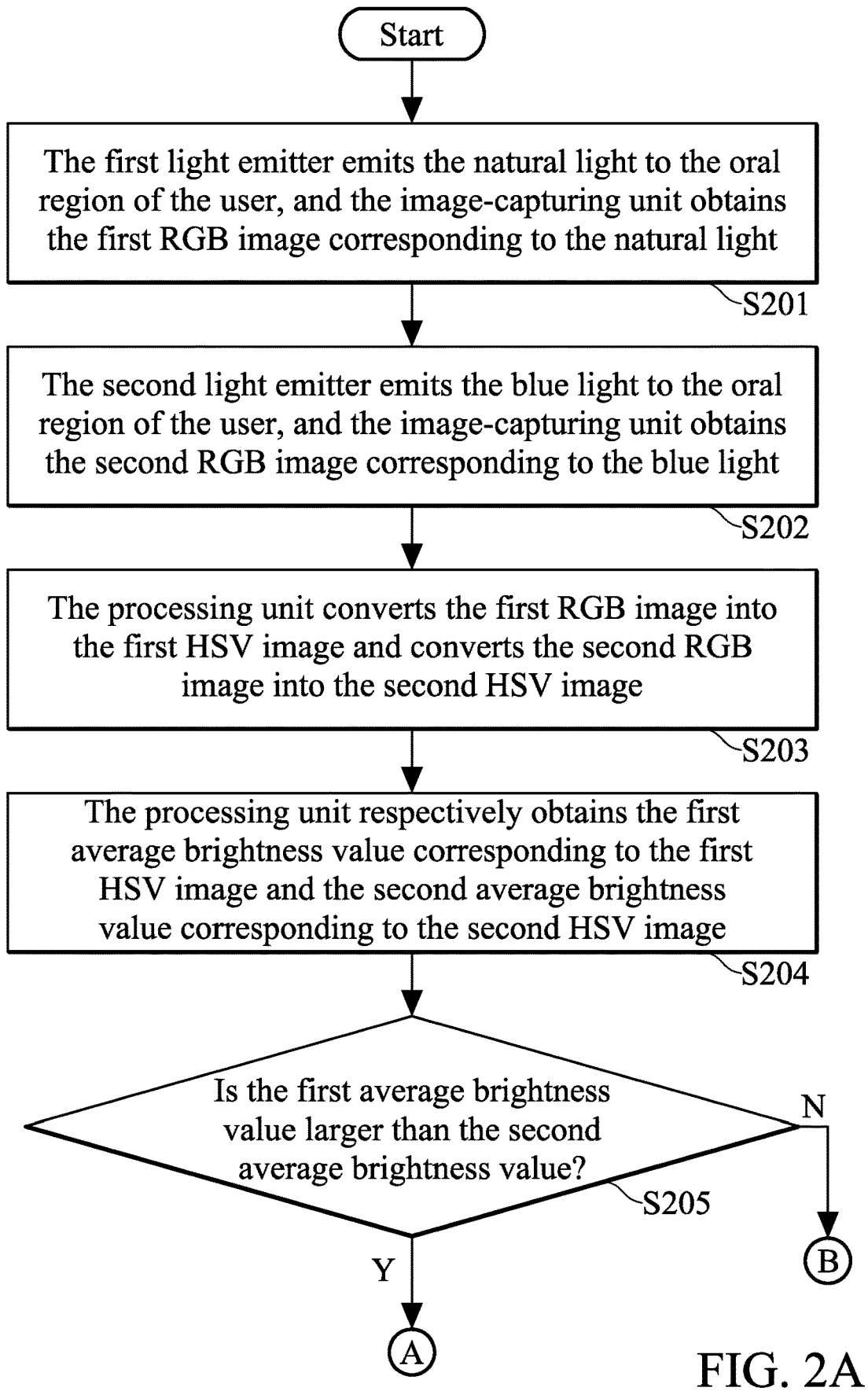
FIGS. 2A-2B are a flowchart of an image-processing method for marking plaque fluorescent reaction areas in accordance with an embodiment of the present invention.
Figure 2B:
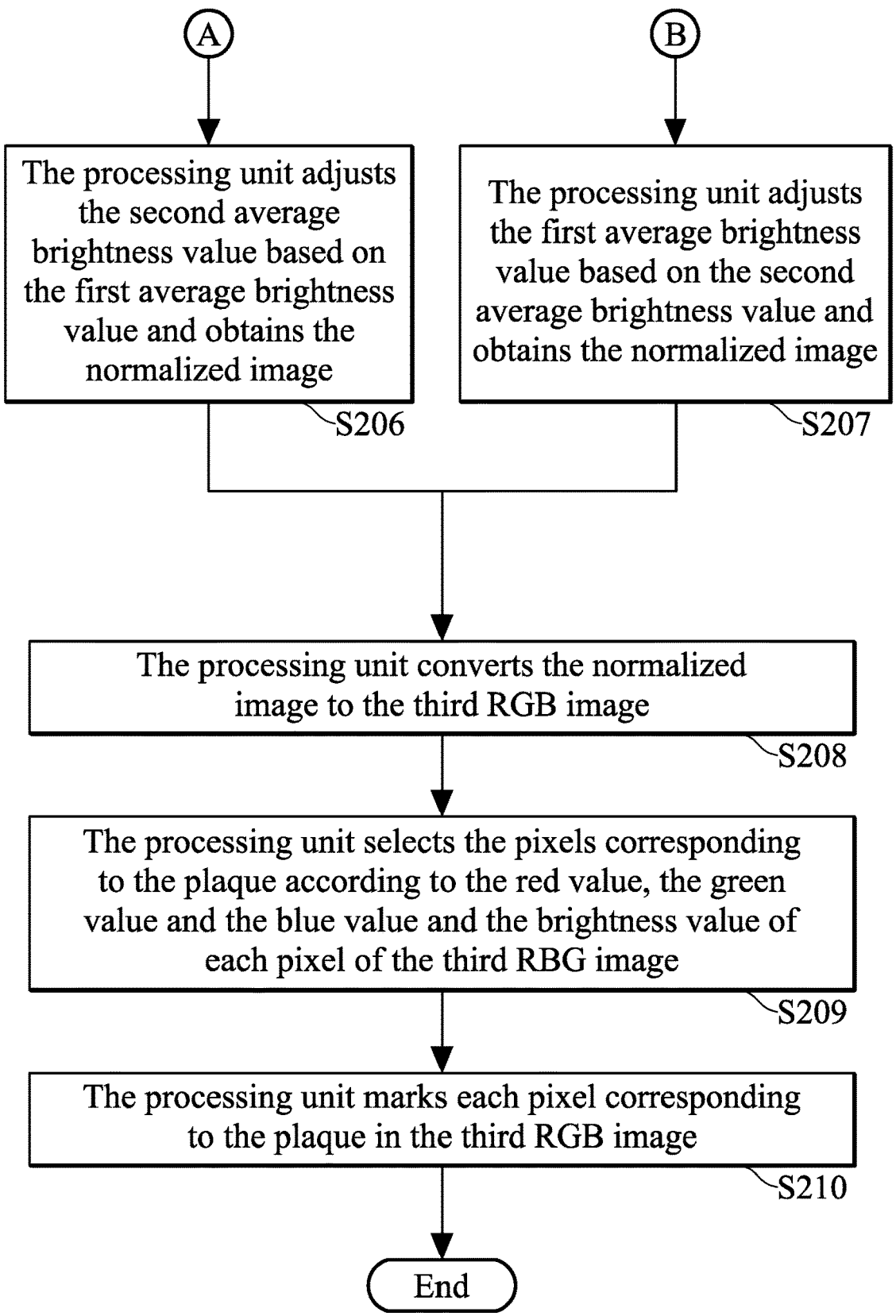

FIGS. 2A-2B are a flowchart of an image-processing method for marking plaque fluorescent reaction areas in accordance with an embodiment of the present invention. In step S201, the first light emitter 110 emits the natural light to the oral region of the user, and the image-capturing unit 130 faces toward the oral region to obtain the first RGB image corresponding to the natural light. In step S202, turning off the first light emitter 110 and turning on the second light emitter 120 to emit the blue light to the oral region of the user, and the image-capturing unit 130 obtains the second RGB image corresponding to the blue light. In step S203, the processing unit 140 converts the first RGB image into the first HSV image and converts the second RGB image into the second HSV image, respectively. In step S204, the processing unit 140 respectively obtains the first average brightness value corresponding to the first HSV image and the second average brightness value corresponding to the second HSV image. In step S205, the processing unit 140 determines which of the first average brightness value and the second average brightness value is larger, and takes the largest one as the basis to adjust another brightness value. When the first average brightness value of the first HSV image corresponding to the natural light is greater than the second average brightness value of the second HSV image corresponding to the blue light, the method proceeds to step S206, and the processing unit 140 adjusts the second average brightness value based on the ratio of the first average brightness value and the second average brightness values, and the predetermined parameter value to increase the brightness value of the second HSV image and obtain the normalized image. On the other hand, when the second average brightness value of the second HSV image corresponding to the blue light is greater than the first average brightness value of the first HSV image corresponding to the natural light, the method proceeds to step S207, the processing unit 140 adjusts the first average brightness value based on the ratio of the second average brightness value and the first average brightness value, and the predetermined parameter value to increase the brightness value of the first HSV image and obtain the normalized image.

Then, after obtaining the normalized image, the method proceeds to step S208, the processing unit 140 converts the normalized image to the third RGB image having the red value, the green value and the blue value to obtain the pixels corresponding to the plaque. In step S209, the processing unit 140 selects the pixels which the red values is greater than the green value and the blue value from all the pixels of the third RBG image, the pixels which the brightness value is greater than the product of the first average brightness value or the second average brightness value and the predetermined parameter value, and the pixels which the red value is greater than the red value of the HSV image with the largest average brightness value, and marks the pixels corresponding to the plaque.

The methods, or certain aspects or portions thereof, may take the form of a program code (i.e., executable instructions) embodied in tangible media, such as floppy diskettes, CD-ROMS, hard drives, or any other machine-readable storage medium, wherein, when the program code is loaded into and executed by a machine, such as a computer, the machine thereby becomes an apparatus for practicing the methods. The methods may also be embodied in the form of a program code transmitted over some transmission medium, such as electrical wiring or cabling, through fiber optics, or via any other form of transmission, wherein, when the program code is received and loaded into and executed by a machine, such as a computer, the machine becomes an apparatus for practicing the disclosed methods. When implemented on a general-purpose processor, the program code combines with the processor to provide a unique apparatus that operates analogously to application specific logic circuits.

As described above, according to the embodiments of the image-processing method for marking plaque fluorescent reaction areas and the system therefor by comparing the brightness values of two images corresponding to different light sources, adjusting the images with the lowest brightness value, and comparing the normalized images with the original RGB images, the feature of the plaque in the image will be more obvious to accurately present the pixels corresponding to the plaque in the image.

It will be apparent to those skilled in the art that various modifications and variations can be made to the structure disclosed without departing from the scope or spirit of the invention. In view of the foregoing, it is intended that the present invention covers modifications and variations of this invention, provided they fall within the scope of the following claims and their equivalents.

What is claimed is:

1. An image-processing method for marking plaque fluorescent reaction areas, comprising:
    emitting, via a first light emitter, natural light to a mouth region of a user;
    obtaining, via an image-capturing unit, a first Red-Green-Blue (RGB) image corresponding to the mouth region;
    emitting, via a second light emitter, blue light to the mouth region;
    obtaining, via the image-capturing unit, a second RGB image corresponding to the mouth region;
    converting, via a processing unit, the first RGB image and the second RGB image into a first Hue-Saturation-Value (HSV) image and a second HSV image respectively;
    obtaining, via the processing unit, a first average brightness value corresponding to the first HSV image and a second average brightness value corresponding to the second HSV image;
    comparing, via the processing unit, the first average brightness value and the second average brightness value to obtain a brightness value of each pixel of one of the first HSV image and the second HSV image, wherein the one of the first HSV image and the second HSV image has the smallest one of the first average brightness value and the second average brightness value;
    multiplying, via the processing unit, a brightness value of each pixel of the one of the first HSV image and the second HSV image by a ratio of the first average brightness value to the second average brightness value and a predetermined parameter value to obtain a normalized image;
    converting, via the processing unit, the normalized image into a third RGB image, and obtaining a plurality of pixel points corresponding to the plaque according to the third RGB image and the first RGB image or the second RGB image; and
    marking the pixel points corresponding to the plaque in the third RGB image and displaying the pixel points corresponding to the plaque in the third RGB image through a specific color value.

2. The image-processing method as claimed in claim 1, wherein the step of obtaining the plurality of pixel points corresponding to the plaque according to the third RGB image and the first RGB image or the second RGB image further comprises:
    determining, via the processing unit, the pixel points corresponding to the plaque according to a red value, a green value and a blue value of each pixel of the third RGB image and a brightness value of each pixel of the normalized image.

3. The image-processing method as claimed in claim 2, wherein the red value corresponding to each of the pixel points of the plaque is greater than a blue value and a green value corresponding to each of the pixel points of the plaque.

4. The image-processing method as claimed in claim 2, wherein the brightness values corresponding to each of the pixel points of the plaque is greater than a product of the largest one of the first average brightness value and the second average brightness value and the predetermined parameter value.

5. The image-processing method as claimed in claim 2, wherein the red value of each of the pixel points corresponding to the plaque in the third RGB image is greater than a red value of the HSV image with the largest one of the first average brightness value and the second average brightness value.

6. A system for marking plaque fluorescent reaction areas, comprising:
   a first light emitter, emitting natural light to a mouth region of a user;
   a second light emitter, emitting blue light to the mouth region;
   an image-capturing unit, obtaining a first Red-Green-Blue (RGB) image corresponding to the natural light and a second RGB image corresponding to the blue light;
   a processing unit, converting the first RGB image into a first Hue-Saturation-Value (HSV) image and the second RGB image into a second HSV image, obtaining a first average brightness value corresponding to the first HSV image and a second average brightness value corresponding to the second HSV image, comparing the first average brightness value and the second average brightness value to obtain a brightness value of each pixel of one of the first HSV image and the second HSV image, wherein the one of the first HSV image and the second HSV image has the smallest one of the first average brightness value and the second average brightness value, multiplying a brightness value of each pixel of the one of the first HSV image and the second HSV image by a ratio of the first average brightness value to the second average brightness value and a predetermined parameter value to obtain a normalized image, converting the normalized image into a third RGB image, and obtaining a plurality of pixel points corresponding to the plaque according to the third RGB image and the first RGB image or the second RGB image; and
   a display unit, displaying and marking the pixel points corresponding to the plaque in the third RGB image and displaying the pixel points corresponding to the plaque in the third RGB image through a specific color value.

7. The system as claimed in claim 6, wherein the processing unit further determines the pixel points corresponding to the plaque according to a red value, a green value and a blue value of each pixel of the third RGB image and a brightness value of each pixel of the normalized image.

8. The system as claimed in claim 7, wherein the red value corresponding to each of the pixel points of the plaque is greater than a blue value and a green value corresponding to each of the pixel points of the plaque.

9. The system as claimed in claim 7, wherein the brightness values corresponding to each of the pixel points of the plaque is greater than the product of the largest one of the first average brightness value and the second average brightness value and the predetermined parameter value.

10. The system as claimed in claim 7, wherein the red value of each of the pixel points corresponding to the plaque in the third RGB image is greater than a red value of the HSV image with the largest one of the first average brightness value and the second average brightness value.

* * * * *